United States Patent
Choi et al.

(10) Patent No.: US 7,943,801 B2
(45) Date of Patent: May 17, 2011

(54) CATALYST COMPOSITION INCLUDING PHOSPHITE LIGANDS AND HYDROFORMYLATION METHOD USING THE SAME

(75) Inventors: Jae-Hui Choi, Daejeon Metropolitan (KR); Dong-Hyun Ko, Daejeon Metropolitan (KR); Sung-Shik Eom, Daejeon Metropolitan (KR); Ji-Joong Moon, Daejeon Metropolitan (KR); Sang-Gi Lee, Daejeon Metropolitan (KR); O-Hark Kwon, Daejeon Metropolitan (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 12/595,074

(22) PCT Filed: Apr. 8, 2008

(86) PCT No.: PCT/KR2008/001985
§ 371 (c)(1),
(2), (4) Date: Oct. 8, 2009

(87) PCT Pub. No.: WO2008/123740
PCT Pub. Date: Oct. 16, 2008

(65) Prior Publication Data
US 2010/0130792 A1 May 27, 2010

(30) Foreign Application Priority Data
Apr. 9, 2007 (KR) .................. 10-2007-0034760

(51) Int. Cl.
*C07C 45/50* (2006.01)
*B01J 31/00* (2006.01)

(52) U.S. Cl. .......... 568/454; 502/152; 502/162
(58) Field of Classification Search .......... 568/454; 502/152, 162
See application file for complete search history.

(56) References Cited

U.S. PATENT DOCUMENTS

| 4,668,651 A | 5/1987 | Billig et al. |
| 4,694,109 A | 9/1987 | Devon et al. |
| 4,769,498 A | 9/1988 | Billig et al. |
| 6,172,267 B1 | 1/2001 | Urata et al. |
| 6,403,837 B1 | 6/2002 | Hess et al. |
| 6,570,033 B2 | 5/2003 | Rottger et al. |
| 6,700,021 B2 | 3/2004 | Bohnen et al. |

FOREIGN PATENT DOCUMENTS

| KR | 19920003119 | 4/1992 |
| KR | 20000053059 A | 8/2000 |
| KR | 20040073919 A | 8/2004 |
| WO | 85/03702 A1 | 8/1985 |
| WO | 98/19990 A1 | 5/1998 |

OTHER PUBLICATIONS

International Search Report, PCT/KR2008/001985, dated Jul. 14, 2008.
Cobley et al., Journal of Organic Chemistry, 69(12); 4031-4040 (2004).
SRI report, November 682; 700A (2002).

*Primary Examiner* — Sikarl A Witherspoon
(74) *Attorney, Agent, or Firm* — Lerner, David, Littenberg, Krumholz & Mentlik, LLP

(57) ABSTRACT

The present invention relates to a catalyst composition that includes a bis-phosphite ligand, a poly-phosphite ligand or a mono-phosphite ligand, and a transition metal catalyst, and a hydroformylation reaction using the same. The catalyst composition has the excellent catalytic activity, and the normal/iso (N/I) selectivity of aldehyde generated by the hydroformylation reaction using the same is increased.

21 Claims, No Drawings

CATALYST COMPOSITION INCLUDING PHOSPHITE LIGANDS AND HYDROFORMYLATION METHOD USING THE SAME

TECHNICAL FIELD

The present invention relates to a catalyst composition that include phosphite ligands that are phosphorus compounds including oxygen, and a hydroformylation process using the same, and more particularly, to a hydroformylation process using a bis-phosphite compound and a poly-phosphite or mono-phosphite compound that are used during a hydroformylation reaction of an olefin compound.

This application claims priority from Korean Patent Application No. 2007-34760 filed on Apr. 9, 2007 in the Korean Intellectual Property Office, the disclosure of which is incorporated herein by reference in its entirety.

BACKGROUND ART

A hydroformylation reaction in which an olefin reacts with a synthesis gas($CO/H_2$) in the presence of a homogeneous organicmetallic catalyst and a ligand to prepare linear (normal) and branched (iso) aldehyde having carbon atoms, the number of which is increased by one was originally discovered by Otto Roelen in Germany in 1938.

In general, the hydroformylation reaction that is known as an oxo react ion is a very important industrial reaction in views of a homogeneous system catalyst reaction, and about 8,400,000 tons of aldehydes including alcohol derivatives were produced by oxo reaction and consumed around the world in 2001 (SRI report, November 2002, 682. 700A).

Various types of aldehydes that are synthesized by the oxo reaction are converted into acids and alcohols that are aldehyde derivatives by using the oxidation process or the hydrogenation process. In addition, aldehydes can also be converted to long alkyl chain-containing acids or alcohols through aldol condensation and then oxidation or reduction.

In particular, hydrogenated alcohol of aldehyde, which is obtained by the oxo reaction, is called oxo alcohol. Oxo alcohol is industrially extensively used as a solvent, an additive, various types of raw materials of plasticizers, synthesis lubricants, and the like.

It is known that a metal carbonyl hydride compound has a catalytic activity of the hydroformylation reaction.

With respect to this, the industrially used catalyst is mainly cobalt (Co) or rhodium (Rh) series. The N/I (ratio of linear (normal) to branched (iso) isomers) selectivity of aldehydes varies according to the type of used catalyst, the type of used ligand and operating conditions.

Currently, in 70% or more oxo plants all over the world, even though there are disadvantages of the costly catalyst and a reduction in catalytic activity due to the poisoning, a low pressure oxo process using a rhodium catalyst and an excessive amount of phosphine ligand is adopted because of the high catalytic activity, the high N/I selectivity, and a relatively easy reaction condition.

In addition to cobalt (Co) and rhodium (Rh), a transit ion metal such as iridium (Ir), ruthenium (Ru), osmium (Os), platinum (Pt), palladium (Pd), iron (Fe), nickel (Ni) and the like may be used as the central metal of the catalyst for oxo reaction. However, in respects to the metals, it is known that the order of the catalytic activity is Rh>>Co>Ir, Ru>Os>Pt>Pd>Fe>Ni. Co, Rh, Pt, and Ru are metal belonging to Group VIII transition metal, and have a high catalytic activity to the oxo reaction. Pt and Ru are used only in a scholarly study, and a current commercial oxo process is based on rhodium and cobalt. Examples thereof may include $HCo(CO)_4$, $HCo(CO)_3PBu_3$ and $HRh(CO)(PR_3)_3$.

Examples of the ligand that is used during the oxo process may include phosphine ($PR_3$, $R=C_6H_5$, and $n-C_4H_9$) phosphine oxide, and phosphite Nitrogen-containing ligands such as amines, amides, or isonitriles have significantly lower catalytic activity as compared to the phosphorus-containing ligands due to their stronger coordination to the metal center. In particular, in the case of when rhodium is used as the central metal, there are few ligands superior to triphenylphosphine (TPP) considering catalytic activity, stability, and costs.

The Eastman Kodak Company and the Union Carbide Company (now, this company is bought by Dow, Co.) have developed a bidentate phosphine ligand and a bisphosphite ligand that have the high catalytic activity and the high N/I selectivity (U.S. Pat. No. 4,694,109, and U.S. Pat. No. 4,668,651). It is known that a bisphosphite ligand developed by the Dow Chemical Company has been used in some plants. Meanwhile, in the case of the poly-phosphite ligand that is represented by the ligand B in Examples 6 to 9 of U.S. Pat. No. 4,668,651, even though the ligand has the very high catalytic activity, the ligand shows very low N/I selectivity. Accordingly, it can be seen that the phosphite ligands have the significantly different catalytic activity and selectivity according to the structure thereof.

The diphosphine xantphos ligand that was developed by Kranenburg, et al, in 1995 is a ligand that is capable of increasing a bite angle between metal and phosphine (P-M-P) by 100° or more, and when the ligand is applied to the hydroformylation reaction, the selectivity to linear aldehyde can be increased, and studies regarding this have been continuously made.

As shown in Korean Patent Application No. 10-2004-73919, the present applicant developed a catalyst system in which a bidentate phosphorus compound containing nitrogen is applied to a transition metal catalyst which exhibits high catalytic activity and N/I selectivity in respects to the hydroformylation reaction.

Commercially, since the value of linear (normal) aldehyde is higher than that of iso aldehyde, there is a need to develop a technology of manufacturing a catalyst that has the excellent catalytic activity and the high N/I selectivity.

DISCLOSURE

Technical Problem

The present invention has been made keeping in mind the above problems occurring in the related art, and it is an object of the present invention to provide a catalyst composition that has the excellent catalytic activity and high normal/iso (N/I) selectivity of produced aldehyde, and a hydroformylation process using the same.

Technical Solution

The present invention provides a catalyst composition that includes a bis-phosphite ligand that is represented by the following Formula 1; a poly-phosphite ligand that is represented by the following Formula 2 or a mono-phosphite ligand that is represented by the following Formula 3; and a transition metal catalyst that is represented by the following Formula 4:

[Formula 1]

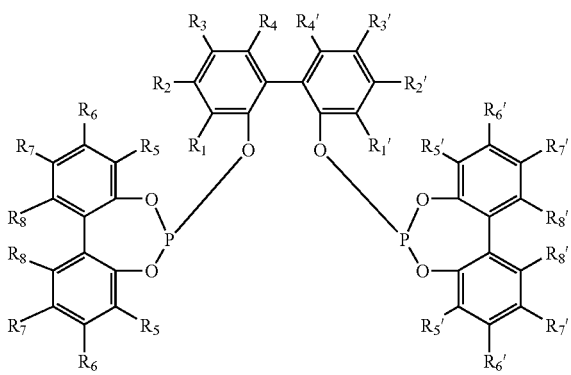

wherein $R_1$ to $R_8$ and $R_1'$ to $R_8'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CONH), nitro group (—NO$_2$), halogen group, cyano group (—CN), silyl group (—SiR$_3$, R is anyone selected from the group consisting of hydrogen, alkyl group and alkoxy group) and sionyl group (—SR, R is anyone selected from the group consisting of hydrogen, alkyl group and alkoxy group),

[Formula 2]

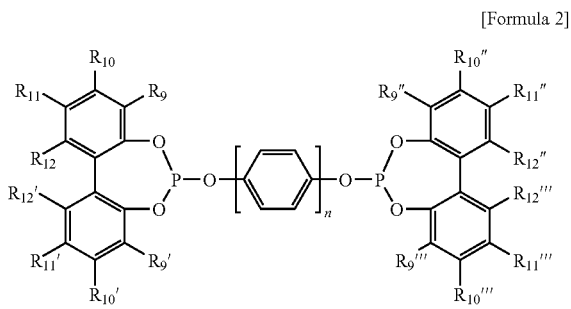

wherein $R_9$ to $R_{12}$, $R_9'$ to $R_{12}'$, $R_9''$ to $R_{12}''$ and $R_9'''$ to $R_{12}'''$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CONH), nitro group (—NO$_2$), halogen group, cyano group (—CN), silyl group (—SiR$_3$, R is anyone selected from the group consisting of hydrogen, alkyl group and alkoxy group) and sionyl group (—SR, R is any one selected from the group consisting of hydrogen, alkyl group and alkoxy group), and n is in the range of 1 to 4,

[Formula 3]

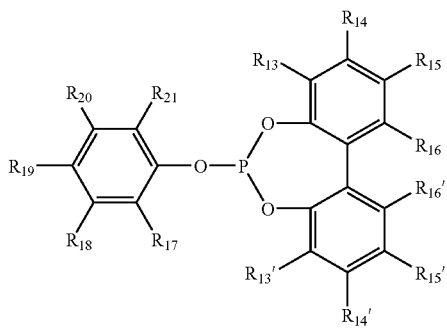

wherein $R_{13}$ to $R_{21}$ and $R_{13}'$ to $R_{16}'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CON), nitro group (—NO$_2$), halogen group, cyano group (—CN), silyl group (—SiR$_3$, R is anyone selected from the group consisting of hydrogen, alkyl group and alkoxy group) and sionyl group (—SR, R is anyone selected from the group consisting of hydrogen, alkyl group and alkoxy group), $$M(L^1)_x(L^2)_y(L^3)_z \quad \text{[Formula 4]}$$

wherein M is any one selected from cobalt (Co), rhodium (Rh) and iridium (Ir), $L^1$, $L^2$ and $L^3$ are each independently any one selected from hydrogen, CO, cyclooctadiene, norbonene, chlorine, triphenylphosphine and acetylacetonato, x, y and z are each independently in the range of 0 to 5, and x, y and z are not 0 at the same time.

The present invention provides a hydroformylation process that includes the steps of a) dissolving a bis-phosphite ligand that is represented by Formula 1 in a solvent to prepare a ligand solution; b) dissolving a poly-phosphite ligand that is represented by Formula 2 or a mono-phosphite ligand that is represented by Formula 3 in a solvent to prepare a ligand solution; c) dissolving a transition metal catalyst that is represented by Formula 4 in a solvent to prepare a catalyst solution; and d) mixing the ligand solutions prepared in the steps a) and b) and the catalyst solution prepared in the step c) to prepare a catalyst composition and adding an olefin compound and a synthesis gas of carbon monoxide and hydrogen to perform the reaction.

Advantageous Effects

In a catalyst composition according to the present invention and a hydroformylation process using the same, a poly-phosphite or mono-phosphite ligand is used in conjunction with a bis-phosphite ligand in a hydroformylation reaction of olefin to obtain the very high catalytic activity and the high N/I selectivity.

BEST MODE

In the present invention, it was found that the catalytic activity and the N/I selectivity are higher in the case of when the poly-phosphite ligand or mono-phosphite ligand are further added as compared to the case of when only the metal catalyst and the bis-phosphite ligand are applied to the hydroformylation reaction of olefin.

Therefore, the present invention provides a catalyst composition that includes a bis-phosphite ligand that is represented by the following Formula 1, a poly-phosphite ligand that is represented by the following Formula 2 or a mono-phosphite ligand that is represented by the following Formula 3, and a transition metal catalyst that is represented by the following Formula 4.

[Formula 1]

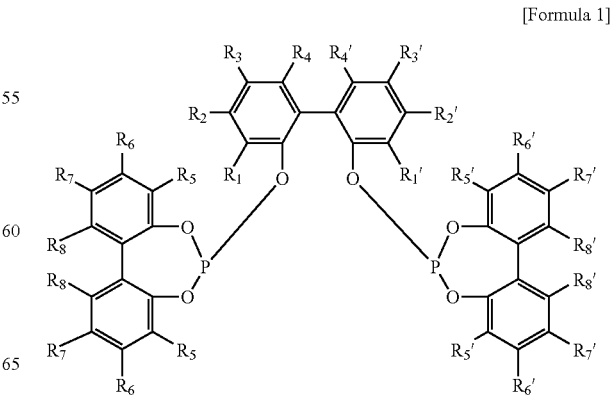

In Formula 1, $R_1$ to $R_8$ and $R_1'$ to $R_8'$ may be each independently different from or the same as each other, and are any one selected from the group consisting of hydrogen, $C_1$ to $C_{20}$ alkyl group, alkoxy group, aryl group, carboalkoxy group, aryloxy group, alkyl carbonyl group, amide group (—COM), nitro group (—$NO_2$), halogen group, cyano group (—CN), silyl group (—$SiR_3$, R is any one selected from the group consisting of hydrogen, alkyl group and alkoxy group) and sionyl group (—SR, R is any one selected from the group consisting of hydrogen, alkyl group and alkoxy group).

[Formula 2]

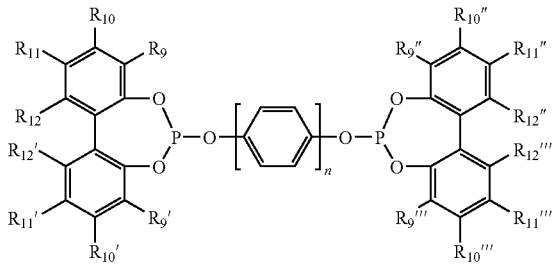

In Formula 2, $R_9$ to $R_{12}$, $R_9'$ to $R_{12}'$, $R_9''$ to $R_{12}''$ and $R_9'''$ to $R_{12}'''$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CONH), nitro group (—$NO_2$), halogen group, cyano group (—CN), silyl group (—$SiR_3$, R is any one selected from the group consisting of hydrogen, alkyl group and alkoxy group) and sionyl group (—SR, R is any one selected from the group consisting of hydrogen, alkyl group and alkoxy group), and n is in the range of 1 to 4.

[Formula 3]

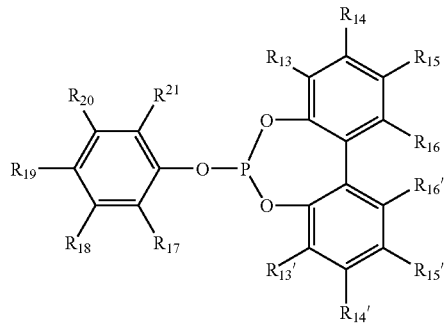

In Formula 3, $R_{13}$ to $R_{21}$ and $R_{13}'$ to $R_{16}'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CONH), nitro group (—$NO_2$), halogen group, cyano group (—CN), silyl group (—$SiR_3$, R is anyone selected from the group consisting of hydrogen, alkyl group and alkoxy group) and sionyl group (—SR, R is any one selected from the group consisting of hydrogen, alkyl group and alkoxy group).

$$M(L^1)_x(L^2)_y(L^3)_z$$ [Formula 4]

In Formula 4, M is any one selected from cobalt (Co), rhodium (Rh) and iridium (Ir), $L^1$, $L^2$ and $L^3$ are each independently any one selected from hydrogen, CO, cyclooctadiene, norbonene, chlorine, triphenylphosphine and acetyl acetonato, x, y and z are each independently in the range of 0 to 5, and x, y and z are not 0 at the same time.

Preferably, there are cases of when $L^1$ is CO, $L^2$ is acetylacetonato, and x and y are 2 and 1, respectively, when $L^1$ is CO, $L^2$ is acetylacetonato, $L^3$ is triphenylphosphine, and x, y, and z are all 1, and when $L^1$ is CO, $L^2$ is hydrogen, $L^3$ is triphenylphosphine, x, y, and z are each independently 1, 1, and 3, but the cases are not limited thereto.

In addition, the present invention provides a hydroformylation process that includes the steps of a) dissolving the bis-phosphite ligand that is represented by Formula 1 in a solvent to prepare a ligand solution; b) dissolving the polyphosphite ligand that is represented by Formula 2 or the mono-phosphite ligand that is represented by Formula 3 in a solvent to prepare a ligand solution; c) dissolving the transition metal catalyst that is represented by Formula 4 in a solvent to prepare a catalyst solution; and d) mixing the ligand solution prepared in the steps a) and b) and the catalyst solution prepared in the step c) to prepare a catalyst composition and adding an olefin compound and a synthesis gas of carbon monoxide and hydrogen to perform the reaction. To be more specific, when the olefin compound and the synthesis gas of carbon monoxide and hydrogen are added, the temperature is increased and pressure is applied while the agitation is performed to prepare aldehyde, thereby providing the hydroformylation process of the olefin compound.

It is preferable that the bis-phosphite ligand be one or more selected from 2,2'-bis(((2,2'-bisphenoxy)phosphino)-oxy)-3,3',5,5'-tetra-tert-butyl-1,1'-biphenyl (ISO-44), and 2,2'-bis (((2,2'-bisphenoxy) phosphino)-oxy)-3,3'-di-tert-butyl-5,5'-di-methoxy-1,1'-biphenyl.

It is preferable that the poly-phosphite ligand be one or more selected from 1,4-bis(((4,4'-dimethoxy-6,6'-di-tort-butyl-2,2'-bisphenoxy)phosphino)oxy)phenyl (Ligand B), 4,4'-Bis(((4,4'-dimethoxy-6,6'-di-tert-butyl-2,2'-bisphenoxy) phosphino)oxy)biphenyl (44-BP), and 1,4-bis(((4,4',6,6'-tetra-tert-butyl-2,2'-bisphenoxy)phosphino)oxy)phenyl.

It is preferable that the mono-phosphite ligand be one or more selected from 4,4'-dimethoxy-6,6'-di-tert-butyl-2,2'-bisphenoxyphosphinoxy-benzene (BPP), 4,4',6,6'-tetra-tert-butyl-2,2'-bisphenoxyphosphinoxy-benzene, 2'-bisphenoxyphosphinoxy-2,6-di-tert-butyl-4-methyl-benzene, and 2,2'-bisphenoxyphosphinoxy-2,6-di-tert-butyl-benzene.

The content of each of the bis-phosphite ligand, the polyphosphite ligand and the mono-phosphite ligand is preferably in the range of 0.5 to 100 mole based on 1 mole of the transition metal catalyst. More preferably, the content may be in the range of 1 to 20 mole.

If the content of the phosphite ligand is less than 0.5 mole, there may be a problem in stability of the catalyst system. On the other hand, if it exceeds 100 moles, the increased use of the expensive ligand without additional benefits may increase process costs.

The transition metal catalyst may include one or more compounds selected from the group consisting of cobalt carbonyl ($Co_2(CO)_8$), acetylacetonato dicarbonyl rhodium (Rh(AcAc)($CO)_2$), acetylacetonato carbonyltriphenylphosphine rhodium (Rh(AcAc)(CO)(TPP)), hydrido carbonyltri(triphenylphosphine) rhodium (HRh(CO)($TPP)_3$), acetylacetonato dicarbonyl iridium (Ir(AcAc)($CO)_2$), and hydrido carbonyl tri(triphenylphosphine) iridium (HIr(CO)($TPP)_3$). In connection with this, it is preferable that the transition metal catalyst be acetylacetonato dicarbonyl rhodium (Rh(AcAc)($CO)_2$).

The content of the transition metal catalyst is calculated by using the content of the free transition metal in the reaction medium of the given hydroformylation process, and the catalyst concentration is desirably in the range of about 10 ppm to about 1000 ppm. In general, the content is in the range of about 10 ppm to 500 ppm, and more preferably 25 to 500 ppm.

In the case of when the content of the transition metal is less than 10 ppm, hydroformylation reaction may be retarded, which restricts industrial application. In the case of when the content of the transition metal is more than 1000 ppm, process costs increase due to the increased use of an expensive transition metal. Furthermore, a reaction rate is not increased in proportion to the increased amount of the transition metal.

In the hydroformylation process, it is preferable that the olefin compound be a compound that is represented by the following Formula 5.

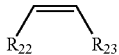

[Formula 5]

In Formula 5, $R_{22}$ and $R_{23}$ are each independently any one selected from the group consisting of hydrogen, an alkyl group having 1 to 20 carbon atoms, a fluorine group (—F), a chlorine group (—Cl), a bromine group (—Br), a trifluoromethyl group (—$CF_3$), and a $C_6$-$C_{20}$ phenyl group having 0 to 5 substituent groups, and the substituent group of the phenyl group may be selected from the group consisting of nitro (—$NO_2$), fluorine (—F), chlorine (—Cl), bromine (—Br), a methyl group, an ethyl group, a propyl group, and a butyl group.

Specifically, the olefin compound may be one or more compounds selected from the group consisting of ethene, propene, 1-butene, 1-pentene, 1-hexene, 1-octene, and styrene.

In the hydroformylation process, examples of the solvent may include one or more compounds selected from the group consisting of aldehydes including propionaldehyde, butyraldehyde, and valeraldehyde; ketones including acetone, methyl ethyl ketone, methyl isobutyl ketone, acetophenone, and cyclohexanone; aromatics including benzene, toluene, and xylene; halogenated aromatics including orthodichlorobenzene; ethers including tetrahydrofuran, dimethoxyethane, and dioxane; halogenated paraffins including methylene chloride; and paraffin hydrocarbons including heptane, and preferably, aldehydes and aromatics including toluene.

In the hydroformylation process, The composition of the syngas (CO/$H_2$) used in the hydroformylation reaction of the present invention may be changed within a broad range. Generally, the molar ratio of CO:$H_2$ is in the range from about 5:95 to 70:30, preferably from about 40:60 to 60:40, particularly preferably about 1:1.

In the hydroformylation process, the hydroformylation reaction is performed at the reaction temperature in the range of preferably about 20 to 180° C., more preferably about 50 to 150° C., and most preferably about 75 to 105° C.

In the above hydroformylation process, the hydroformylation process is performed at the reaction pressure in the range of preferably about 1 to 700 bar, and more preferably about 1 to 300 bar.

The reaction caused by the hydroformylation process may be shown in the following Reaction Equation 1 or Reaction Equation 2.

[Reaction Equation 1]

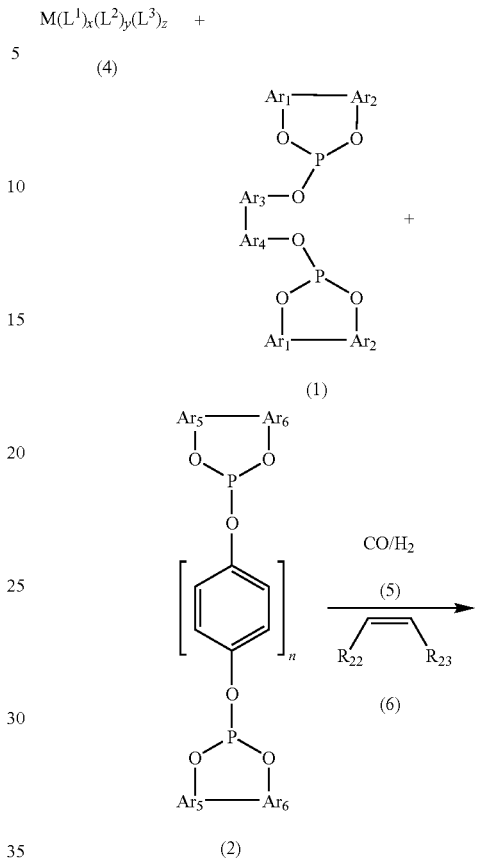

[Reaction Equation 2]

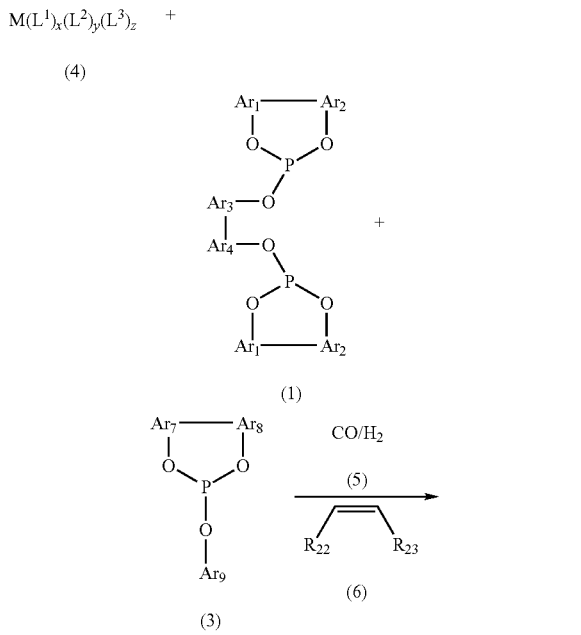

-continued

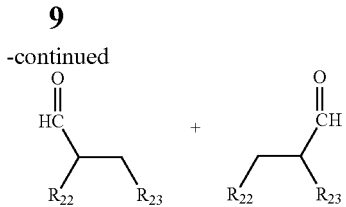

In Reaction Equation 1 and Reaction Equation 2, $Ar_1$ to $Ar_9$ are a substituted or unsubstituted benzene ring, and $R_{22}$ and $R_{23}$ are the same as those defined in Formula 5.

In order to perform the hydroformylation reaction, first, the transition metal catalyst 4, and the ligands 1 and 2 or 3 are dissolved in a solvent such as benzene, toluene, ethanol, pentanol, octanol, texanol, butyraldehyde, and pentylaldehyde to prepare a solution mixture of the catalyst and the ligands.

In the reaction, the bis-phosphite ligand 1 and the poly-phosphite 2 or the mono-phosphite ligand 3 are mixed with each other and used as the ligand.

The olefin compound 6, and the synthesis gas 5 of carbon monoxide and hydrogen are injected in conjunction with the solution mixture of the catalyst and the ligands into the reactor, agitated, heated and pressurized to perform the hydroformylation reaction.

MODE FOR INVENTION

Hereinafter, the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

EXAMPLES 1 TO 4

The hydroformylation reaction of propene using the acetylacetonato dicarbonyl rhodium $(Rh(AcAc)(CO)_2)$ catalyst, the bis-phosphite compound, and the poly-phosphite compound 0.100 mg of $Rh(AcAc)(CO)_2$ (0.390 mmol) that was the catalyst, 0.2 in of hexadecane that was the internal standard substance for GC analysis, and ISO-44 that was the bis-phosphite compound and Ligand B or 44-BP that was the poly-phosphite compound were dissolved in the toluene solvent according to the molar ratio (L/Rh) of the ligand to rhodium $(Rh(AcAc)(CO)_2)$ described in Table 1 in the high throughput screen unit (HTS) that was manufactured by Auto Clave, Co., Ltd. so that the total volume of the solution was 100 ml, and then added.

The reaction gas was injected into the reaction solution so that the molar ratio of propene (olefin):CO:$H_2$ was 1:1:1, and the reaction was performed for 2.5 hours while the pressure in the reactor was maintained at 6 bar and the agitation was performed at 85° C.

The types of the catalyst and the ligand to the above reaction, the molar ratio of the ligand to the catalyst, the N/I selectivity, and the catalytic activity are described in Table 1 in detail.

In Examples and Comparative Examples of the present invention, the N/I selectivity value is the production ratio of normal-butyraldehyde to iso-butyraldehyde. The production amount of each aldehyde was calculated based on the amount of hexadecane used as the internal standard for the GC analysis.

The catalytic activity was obtained by dividing the total amount of normal-butyraldehyde and iso-butyraldehyde produced by the molecular weight of butyraldehyde, the concentration of the used catalyst, and the reaction time. The unit of the catalytic activity was $mol_{(BAL)}/mol_{(Rh)}/h$.

TABLE 1

| Comparison | Catalyst | L1 | L2 | L1/Rh mol/mol | L2/Rh mol/mol | N/I | Catalytic activity ($mol_{(BAL)}$/$mol_{(Rh)}$/h) |
|---|---|---|---|---|---|---|---|
| Example 1 | $Rh(AcAc)(CO)_2$ | ISO-44 | Ligand B | 5 | 3 | 18.3 | 306.0 |
| Example 2 | $Rh(AcAc)(CO)_2$ | ISO-44 | Ligand B | 5 | 5 | 16.7 | 307.7 |
| Example 3 | $Rh(AcAc)(CO)_2$ | ISO-44 | 44-BP | 5 | 3 | 13.5 | 308.6 |
| Example 4 | $Rh(AcAc)(CO)_2$ | ISO-44 | 44-BP | 5 | 5 | 16.1 | 292.9 |

L1: bis-phosphite compound,
L2: poly-phosphite compound

EXAMPLES 5 AND 6

The hydroformylation reaction of propene using the acetylacetonato dicarbonyl rhodium $(Rh(AcAc)(CO)_2)$ catalyst, the bis-phosphite compound, and the mono-phosphite compound The catalytic activity test was performed by using the same process as Examples 1 to 4 according to the molar ratio described in the following Table 2, except that ISO-44 that was the bis-phosphite compound and BPP that was the monophosphite compound were used as the ligand, and the results are described in the following Table 2.

TABLE 2

| Comparison | Catalyst | L1 | L2 | L1/Rh mol/mol | L2/Rh mol/mol | N/I | Catalytic activity ($mol_{(BAL)}$/$mol_{(Rh)}$/h) |
|---|---|---|---|---|---|---|---|
| Example 5 | $Rh(AcAc)(CO)_2$ | ISO-44 | BPP | 5 | 5 | 15.0 | 350.3 |
| Example 6 | $Rh(AcAc)(CO)_2$ | ISO-44 | BPP | 5 | 15 | 16.6 | 285.5 |

L1: bis-phosphite compound,
L2: mono-phosphite compound

EXAMPLES 7 TO 14

The hydroformylation reaction of propene using the acetylacetonato dicarbonyl rhodium (Rh(AcAc)(CO)$_2$) catalyst, the bis-phosphite compound, and the poly-phosphite compound according to a change in temperature The catalytic activity test was performed by using the same process as Examples 1 to 4 according to the molar ratio described in the following Table 3, except that the compound described in the following Table 3 was used as the ligand, the molar ratio of rhodium (Rh(AcAc)(CO)$_2$) to the ligand was fixed to 5, and the react ion temperature was changed in the range of 75° C. to 105° C. by 10° C., and the results are described in the following Table 3.

TABLE 3

| Catalyst | L1 | L2 | L1/Rh mol/mol | L2/Rh mol/mol | Temperature (° C.) | N/I | Catalytic Activity (mol$_{(BAL)}$/ (mol$_{(Rh)}$/h) |
|---|---|---|---|---|---|---|---|
| Example 7 | Rh(AcAc)(CO)$_2$ | ISO-44 | Ligand B | 5 | 5 | 75 | 24.0 | 286.5 |
| Example 8 | Rh(AcAc)(CO)$_2$ | ISO-44 | Ligand B | 5 | 5 | 85 | 16.5 | 306.8 |
| Example 9 | Rh(AcAc)(CO)$_2$ | ISO-44 | Ligand B | 5 | 5 | 95 | 8.1 | 309.0 |
| Example 10 | Rh(AcAc)(CO)$_2$ | ISO-44 | Ligand B | 5 | 5 | 105 | 5.0 | 275.2 |
| Example 11 | Rh(AcAc)(CO)$_2$ | ISO-44 | 44-BP | 5 | 5 | 75 | 21.2 | 273.8 |
| Example 12 | Rh(AcAc)(CO)$_2$ | ISO-44 | 44-BP | 5 | 5 | 85 | 16.5 | 297.6 |
| Example 13 | Rh(AcAc)(CO)$_2$ | ISO-44 | 44-BP | 5 | 5 | 95 | 11.0 | 305.1 |
| Example 14 | Rh(AcAc)(CO)$_2$ | ISO-44 | 44-BP | 5 | 5 | 105 | 6.7 | 281.6 |

L1: bis-phosphite compound,
L2: poly-phosphite compound

EXAMPLES 15 TO 18

The hydroformylation reaction of propene using the acetylacetonato dicarbonyl rhodium (Rh(AcAc)(CO)$_2$) catalyst, the bis-phosphite compound, and the mono-phosphite compound according to a change in temperature The catalytic activity test was performed by using the same process as Examples 7 to 10, except that ISO-44 that was the bis-phosphite compound and BPP that was the mono-phosphite compound were used as the ligand, and the results are described in Table 4.

TABLE 4

| Catalyst | L1 | L2 | L1/Rh mol/mol | L2/Rh mol/mol | Temperature (° C.) | N/I | Catalytic Activity (mol$_{(BAL)}$/ (mol$_{(Rh)}$/h) |
|---|---|---|---|---|---|---|---|
| Example 15 | Rh(AcAc)(CO)$_2$ | ISO-44 | BPP | 5 | 5 | 75 | 18.3 | 305.7 |
| Example 16 | Rh(AcAc)(CO)$_2$ | ISO-44 | BPP | 5 | 5 | 85 | 15.9 | 345.0 |
| Example 17 | Rh(AcAc)(CO)$_2$ | ISO-44 | BPP | 5 | 5 | 95 | 9.9 | 348.2 |
| Example 18 | Rh(AcAc)(CO)$_2$ | ISO-44 | BPP | 5 | 5 | 105 | 6.1 | 317.3 |

L1: bis-phosphite compound,
L2: mono-phosphite compound

COMPARATIVE EXAMPLES 1 TO 3

The hydroformylation reaction of propene using the acetylacetonato dicarbonyl rhodium (Rh(AcAc)(CO)$_2$) catalyst, and 2,2'-bis(((2,2'-bisphenoxy)phosphino)-oxy)-3,3',5,5'-tetra-tert-butyl-1,1'-biphenyl (ISO-44)

The catalytic activity test was performed by using the same process as Example 1, except that 130-44 was used as the ligand and the molar ratio of rhodium (Rh(AcAc)(CO)$_2$) to the ligand was 2, 5, and 10, and the results are described in the following Table 5.

COMPARATIVE EXAMPLES 4 AND 5

The hydroformylation reaction of propene using the acetylacetonato dicarbonyl rhodium (Rh(AcAc)(CO)$_2$) catalyst and 1,4-bis(((4,4'-dimethoxy-6,6'-di-tert-butyl-2,2'-bisphenoxy)phosphino)oxy)phenyl (Ligand B)

The catalytic activity test was performed by using the same process as Comparative Example 1, except that Ligand B was used instead of ISO-44 as the ligand and the molar ratio of rhodium (Rh(AcAc)(CO)$_2$) to the ligand was 3 and 10, and the results are described in the following Table 5.

COMPARATIVE EXAMPLES 6 AND 7

The hydroformylation reaction of propene using the acetylacetonato dicarbonyl rhodium (Rh(AcAc)(CO)$_2$) and 4,4'-bis(((4,4'-dimethoxy-6,6'-di-tert-butyl-2,2'-bisphenoxy)phosphino)oxy)biphenyl (44-BP)

The catalytic activity test was performed by using the same process as Comparative Examples 2 and 3, except that 44-BP was used instead of ISO-44 as the ligand, and the results are described in the following Table 5.

COMPARATIVE EXAMPLES 8 AND 9

The hydroformylation reaction of propene using the acetylacetonato dicarbonyl rhodium (Rh(AcAc)(CO)$_2$) and 4,4'-dimethoxy-6,6'-di-tert-butyl-2,2'-bisphenoxyphosphinoxybenzene (BPP)

The catalytic activity test was performed by using the same process as Comparative Examples 2 and 3, except that BPP was used instead of ISO-44 as the ligand, and the results are described in the following Table 5.

TABLE 5

| Division | Catalyst | Ligand (L) | L/Rh mol/mol | N/I | Catalytic activity (mol$_{(BAL)}$/mol$_{(Rh)}$/h) |
|---|---|---|---|---|---|
| Comparative Example 1 | Rh(AcAc)(CO)$_2$ | ISO-44 | 2 | 10.5 | 289.2 |
| Comparative Example 2 | Rh(AcAc)(CO)$_2$ | ISO-44 | 5 | 9.6 | 271.9 |
| Comparative Example 3 | Rh(AcAc)(CO)$_2$ | ISO-44 | 10 | 10.4 | 265.2 |
| Comparative Example 4 | Rh(AcAc)(CO)$_2$ | Ligand B | 3 | 1.1 | 236.3 |
| Comparative Example 5 | Rh(AcAc)(CO)$_2$ | Ligand B | 10 | 1.3 | 197.2 |
| Comparative Example 6 | Rh(AcAc)(CO)$_2$ | 44-BP | 5 | 1.0 | 262.2 |
| Comparative Example 7 | Rh(AcAc)(CO)$_2$ | 44-BP | 10 | 1.1 | 246.0 |
| Comparative Example 8 | Rh(AcAc)(CO)$_2$ | BPP | 5 | 1.0 | 355.6 |
| Comparative Example 9 | Rh(AcAc)(CO)$_2$ | BPP | 10 | 1.0 | 304.8 |

COMPARATIVE EXAMPLES 10 TO 17

The hydroformylation reaction of propene using the acetylacetonato dicarbonyl rhodium (Rh(AcAc)(CO)$_2$) catalyst, and the bis-phosphite compound according to a change in temperature The catalytic activity test was performed by using the same process as Examples 7 to 10, except that only ISO-44 that was the bis-phosphite compound was used as the ligand and the molar ratio of rhodium (Rh(AcAc)(CO)$_2$) to the ligand was 5 and 10, and the results are described in the following Table 6.

COMPARATIVE EXAMPLES 18 TO 21

The hydroformylation reaction of propene using the acetylacetonato dicarbonyl rhodium (Rh(AcAc)(CO)$_2$) catalyst, and the poly-phosphite compound according to a change in temperature The catalytic activity test was performed by using the same process as Examples 7 to 10, except that only 44-BP that was the poly-phosphite compound was used as the ligand, and the results are described in the following Table 6.

COMPARATIVE EXAMPLES 22 TO 25

The hydroformylation reaction of propene using the acetylacetonato dicarbonyl rhodium (Rh(AcAc)(CO)$_2$) catalyst, and the mono-phosphite compound according to a change in temperature The catalytic activity test was performed by using the same process as Examples 7 to 10, except that only BPP that was the mono-phosphite compound was used as the ligand, and the results are described in the following Table 6.

TABLE 6

| | Catalyst | Ligand (L) | L/Rh mol/mol | Temperature (° C.) | N/I | Catalytic activity (mol$_{(BAL)}$/mol$_{(Rh)}$/h) |
|---|---|---|---|---|---|---|
| Comparative Example 10 | Rh(AcAc)(CO)$_2$ | ISO-44 | 5 | 75 | 14.5 | 285.0 |
| Comparative Example 11 | Rh(AcAc)(CO)$_2$ | ISO-44 | 5 | 80 | 9.5 | 270.8 |
| Comparative Example 12 | Rh(AcAc)(CO)$_2$ | ISO-44 | 5 | 95 | 7.3 | 281.3 |
| Comparative Example 13 | Rh(AcAc)(CO)$_2$ | ISO-44 | 5 | 105 | 4.4 | 269.7 |
| Comparative Example 14 | Rh(AcAc)(CO)$_2$ | ISO-44 | 10 | 75 | 16.2 | 275.8 |
| Comparative Example 15 | Rh(AcAc)(CO)$_2$ | ISO-44 | 10 | 80 | 10.5 | 259.0 |
| Comparative Example 16 | Rh(AcAc)(CO)$_2$ | ISO-44 | 10 | 95 | 7.4 | 258.8 |
| Comparative Example 17 | Rh(AcAc)(CO)$_2$ | ISO-44 | 10 | 105 | 4.5 | 223.8 |
| Comparative Example 18 | Rh(AcAc)(CO)$_2$ | 44-BP | 5 | 75 | 1.0 | 246.4 |
| Comparative Example 19 | Rh(AcAc)(CO)$_2$ | 44-BP | 5 | 80 | 1.0 | 270.8 |
| Comparative Example 20 | Rh(AcAc)(CO)$_2$ | 44-BP | 5 | 95 | 1.2 | 285.4 |
| Comparative Example 21 | Rh(AcAc)(CO)$_2$ | 44-BP | 5 | 105 | 1.2 | 303.1 |
| Comparative Example 22 | Rh(AcAc)(CO)$_2$ | BPP | 5 | 75 | 1.2 | 271.6 |
| Comparative Example 23 | Rh(AcAc)(CO)$_2$ | BPP | 5 | 80 | 1.0 | 350.7 |
| Comparative Example 24 | Rh(AcAc)(CO)$_2$ | BPP | 5 | 95 | 1.1 | 413.7 |
| Comparative Example 25 | Rh(AcAc)(CO)$_2$ | BPP | 5 | 105 | 1.1 | 323.1 |

If Examples and Comparative Examples were compared to each other, it could be seen that in the case of when the bis-phosphite compound and the poly-phosphite ligand or the mono-phosphite ligand were simultaneously mixed with each other, the very high catalytic activity was maintained, and the N/I selectivity was 1.9 times higher than that of the case of when only the bis-phosphite was used.

In the case of Example 1, in the case of when acetylacetonato dicarbonyl rhodium (Rh(AcAc)(CO)$_2$) was used as the catalyst, 1,4-bis(((4,4'dimethoxy-6,6'-di-tert-butyl-2,2'-bisphenoxy)phosphino) oxy)phenyl (Ligand B) was added, and 2,2'-bis(((2,2'-bisphenoxy)phosphino)-oxy)-3,3',5,5'-tetra-tert-butyl-1,1'-biphenyl (ISO-44) was further added, the catalytic activity was 306 mol$_{(BAL)}$/mol$_{(Rh)}$/h, and the N/I selectivity was 18.3.

However, in the case of Comparative Example 2 in which only ISO-44 was used under the same condition, the catalytic activity was 271.9 mol$_{(BAL)}$/mol$_{(Rh)}$/h, and the N/I selectivity was 9.6.

In addition, it could be seen that in the case of when two ligands were simultaneously used like Examples 1 to 18, the N/I selectivity was higher at the same temperature condition as compared to the case of when only ISO-44 was used.

With respect to the results of Comparative Examples 1 and 2 in which the bis-phosphite compound was used, as shown in Table 5, in the case of when ISO-44 was used as the ligand, when the ratio of rhodium to ISO-44 was 2 mole or more, the catalytic activity was 260 mol$_{(BAL)}$/mol$_{(Rh)}$/h or more which was the high value. In this case, the N/I selectivity was about 10, which was the slightly low selectivity to normal-aldehyde.

With respect to the catalytic activity and the N/I selectivity in respects to the hydroformylation reaction of propene of the poly-phosphite and the mono-phosphite used in Comparative Examples 4, 6 and 8, all three ligands had the low N/I selectivity of about 1 and the catalytic activity in the range of 230 to 360 mol$_{(BAL)}$/mol$_{(Rh)}$/h.

In addition, Comparative Examples 3, 5, 7, 9 and 14 to 17 in which one type of ligand was used and the molar ratio of rhodium (Rh(AcAc)(CO)$_2$) to the ligand was 10 were compared to Examples 1 to 18 in which two types of ligands were used and the sum total of the molar ratios of rhodium (Rh(AcAc)(CO)$_2$) to the ligands was 8 or more. In Comparative Examples 3, 5, 7, 9 and 14 to 17, even though one type of ligand was used in a great amount like Examples 1 to 18, as shown in Table 5 and Table 6, it could be seen that only the activity was reduced while the WI selectivity was insignificantly improved. Accordingly, it could be seen that even though one type of ligand was used in a great amount, the effect that was obtained in Examples 1 to 18, in which two types of ligands were used, according to the present invention was not provided.

The invention claimed is:

1. A catalyst composition comprising:
   a bis-phosphite ligand that is represented by the following Formula 1;
   a poly-phosphite ligand that is represented by the following Formula 2 or a mono-phosphite ligand that is represented by the following Formula 3; and
   a transition metal catalyst that is represented by the following Formula 4:

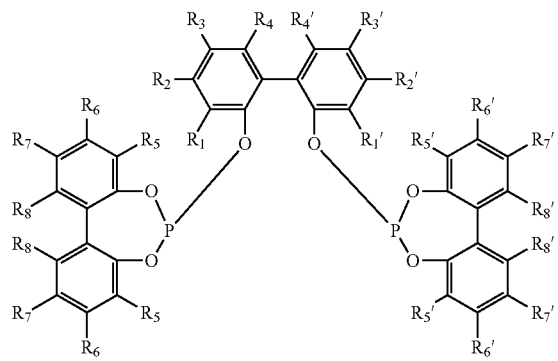

Formula 1 wherein $R_1$ to $R_8$ and $R_1'$ to $R_8'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —NO$_2$, halogen group, cyano group represented by the following formula —CN, silyl group represented by the following formula —SiR$_3$, wherein R is any one selected from the group consisting of hydrogen, alkyl group and alkoxy group, and sionyl group represented by the following formula —SR, wherein R is any one selected from the group consisting of hydrogen, alkyl group and alkoxy group,

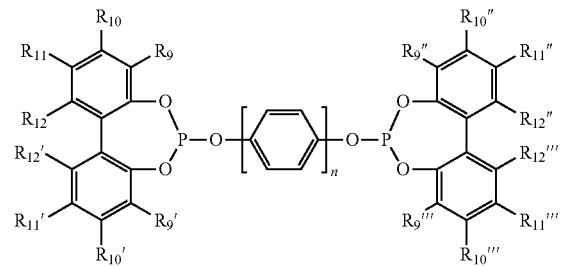

Formula 2 wherein $R_9$ to $R_{12}$, $R_9'$ to $R_{12}'$, $R_9''$ to $R_{12}''$ and $R_9'''$ to $R_{12}'''$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —NO$_2$, halogen group, cyano group represented by the following formula —CN, silyl group represented by the following formula —SiR$_3$, wherein R is any one selected from the group consisting of hydrogen, alkyl group and alkoxy group, and sionyl group represented by the following formula —SR, wherein R is any one selected from the group consisting of hydrogen, alkyl group and alkoxy group, and n is in the range of 1 to 4, Formula 3

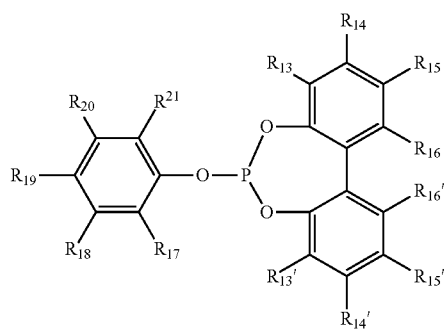

wherein $R_{13}$ to $R_{21}$ and $R_{13}'$ to $R_{16}'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —$NO_2$, halogen group, cyano group represented by the following formula —CN, silyl group represented by the followin formula —$SiR_3$, wherein R is any one selected from the group consisting of hydrogen, alkyl group and alkoxy group and sionyl group represented by the following formula —SR, wherein R is any one selected from the group consisting of hydrogen, alkyl group and alkoxy group, Formula 4

$M(L^1)_x(L^2)_y(L^3)_z$ wherein M is any one selected from cobalt (Co), rhodium (Rh) and iridium (Ir), $L^1, L^2$ and $L^3$ are each independently any one selected from hydrogen, CO, cyclooctadiene, norbonene, chlorine, triphenylphosphine and acetylacetonato, x, y and z are each independently in the range of 0 to 5, and x, y and z are not 0 at the same time.

2. The catalyst composition as set forth in claim 1, wherein the content of the transition metal catalyst is calculated by using the content of a free transition metal in a reaction medium, and the content of the free transition metal is in the range of 25 to 500 ppm.

3. The catalyst composition as set forth in claim 1, wherein the content of each of the bis-phosphite ligand, the poly-phosphite ligand, and the mono-phosphite ligand is in the range of 0.5 to 100 mole based on 1 mole of the transition metal catalyst.

4. The catalyst composition as set forth in claim 1, wherein the bis-phosphite ligand includes one or more selected from the group consisting of 2,2'-bis(((2,2'-bisphenoxy) phosphino)-oxy)-3,3',5,5'-tetra-tert-butyl-1,1'-biphenyl (ISO-44) and 2,2'-bis(((2,2'-bisphenoxy)phosphino)-oxy)-3,3'-di-tert-butyl-5,5'-di-methoxy-1, 1'-biphenyl.

5. The catalyst composition as set forth in claim 1, wherein the poly-phosphite ligand includes one or more selected from the group consisting of 1,4-bis(((4,4'-dimethoxy-6,6'-di-tert-butyl-2,2'-bisphenoxy)phosphino)oxy)phenyl (Ligand B), 4,4'-Bis (((4,4'-dimethoxy-6,6'-di-tert-butyl-2,2'-bisphenoxy) phosphino)oxy)biphenyl (44-BP), and 1,4-bis( ((4,4', 6,6'-tetra-tert-butyl-2,2'-bisphenoxy)phosphino)oxy)phenyl.

6. The catalyst composition as set forth in claim 1, wherein the mono-phosphite ligand includes one or more selected from the group consisting of 4,4'-dimethoxy-6,6'-di-tert-butyl-2,2'-bisphenoxyphosphinoxy-benzene (BPP), 4,4' ,6,6'-tetra-tert-butyl-2,2'-bisphenoxyphosphinoxy-benzene, 2,2'-bisphenoxyphosphinoxy-2,6-di-tert-butyl-4-methyl-benzene and 2,2'-bisphenoxyphosphinoxy-2,6-di-tert-butyl-benzene.

7. The catalyst composition as set forth in claim 1, wherein the transition metal catalyst includes one or more compounds selected from the group consisting of cobalt carbonyl (Co(CO)$_8$), acetylacetonato dicarbonyl rhodium (Rh(AcAc)(CO)$_2$), acetylacetonato carbonyltriphenylphosphine rhodium (Rh(AcAc)(CO)(TPP)), hydrido carbonyltri(triphenylphosphine) rhodium (HRh(CO)(TPP)$_3$), acetylacetonato dicarbonyl iridium (Ir(AcAc)(CO)$_2$), and hydrido carbonyl tri(triphenylphosphine) iridium (HIr(CO)(TPP)$_3$).

8. A hydroformylation process comprising the steps of:
a) dissolving a bis-phosphite ligand that is represented by the following Formula 1 in a solvent to prepare a ligand solution;
b) dissolving a poly-phosphite ligand that is represented by Formula 2 or a mono-phosphite ligand that is represented by the following Formula 3 in a solvent to prepare a ligand solution;
c) dissolving a transition metal catalyst that is represented by the following Formula 4 in a solvent to prepare a catalyst solution; and
d) mixing the ligand solutions prepared in the steps a) and b) and the catalyst solution prepared in the step c) to prepare a catalyst composition and adding an olefin compound and a synthesis gas of carbon monoxide and hydrogen to perform the reaction, Formula 1

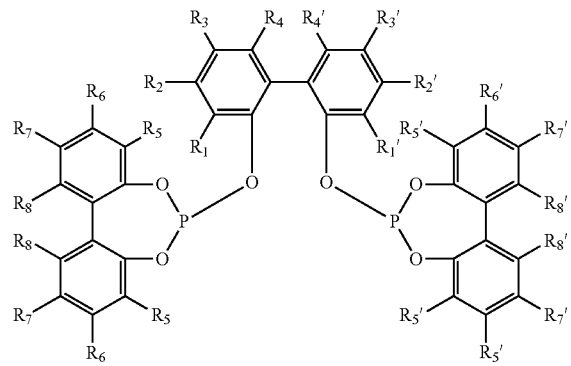

wherein $R_1$ to $R_8$ and $R_1'$ to $R_8'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —$NO_2$, halogen group, cyano group represented. by the following formula —CN, silyl group represented by the following formula —$SiR_3$, wherein R is any one selected from the group consisting of hydrogen, alkyl group and alkoxy group, and sionyl group represented by the following formula —SR, wherein R is any one selected from the group consisting of hydrogen, alkyl group and alkoxy group,

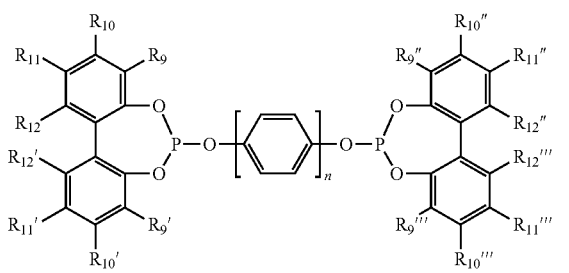

Formula 2 wherein $R_9$ to $R_{12}$, $R_9'$ to $R_{12}'$, $R_9''$ to $R_{12}''$ and $R_9'''$ to $R_{12}'''$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group (—CONH), nitro group represented by the following formula —$NO_2$, halogen group, cyano group represented by the following formula —CN, silyl group represented by the followinq formula —$SiR_3$, wherein R is any one selected from the group consisting of hydrogen, alkyl group and alkoxy group and sionyl group represented by the following formula —SR, wherein R is any one selected from the group consisting of hydrogen, alkyl group and alkoxy group, and n is in the range of 1 to 4,

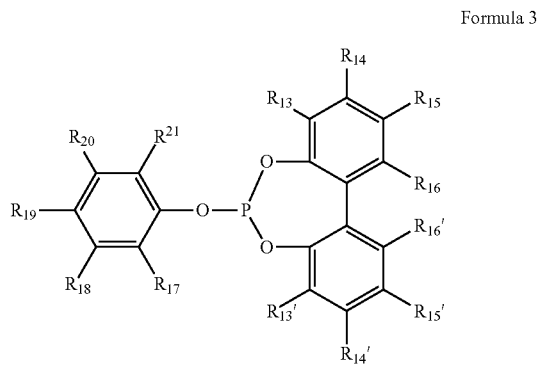

Formula 3 wherein $R_{13}$ to $R_{21}$ and $R_{13}'$ to $R_{16}'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —$NO_2$, halogen group, cyano group represented by the following formula —CN, silyl group represented by the following formula —$SiR_3$, wherein R is any one selected from the group consisting of hydrogen, alkyl group and alkoxy group and sionyl group represented by the following formula —SR, wherein R is any one selected from the group consisting of hydrogen, alkyl group and alkoxy group, Formula 4

$M (L^1)_x (L^2)_y (L^3)_z$ wherein M is any one selected from cobalt (Co), rhodium (Rh) and iridium (Ir), $L^1, L^2$ and $L^3$ are each independently any one selected from hydrogen, CO, cyclooctadiene, norbornene, chlorine, triphenylphosphine and acetylacetonato, x, y and z are each independently in the range of 0 to 5, and x, y and z are not 0 at the same time.

9. The hydroformylation process as set forth in claim 8, wherein the content of the transition metal catalyst is calculated by using the content of a free transition metal in a reaction medium of the catalyst composition prepared in the step d), and the content of the free transition metal is in the range of 25 to 500 ppm.

10. The hydroformylation process as set forth in claim 8, wherein the content of each of the bis-phosphite ligand, the poly-phosphite ligand, and the mono-phosphite ligand is in the range of 0.5 to 100 mole based on 1 mole of the transition metal catalyst.

11. The hydroformylation process as set forth in claim 8, wherein the bis-phosphite ligand includes one or more selected from the group consisting of 2,2'-bis(((2,2'-bisphenoxy) phosphino)-oxy)-3,3' ,5,5'-tetra-tert-butyl-1, 1'-biphenyl (ISO-44) and 2,2'-bis(((2,2'-bisphenoxy)phosphino)-oxy)-3,3'-di-tert-butyl-5,5'-di-methoxy-1, 1'-biphenyl.

12. The hydroformylation process as set forth in claim 8, wherein the poly-phosphite ligand includes one or more selected from the group consisting of 1,4-bis(((4,4'-dimethoxy-6,6'-di-tert-butyl-2,2'-bisphenoxy)phosphino) oxy)phenyl (Ligand B) ,4,4'-Bis(((4,4'-dimethoxy-6,6'-di-tert-butyl-2,2'-bisphenoxy) phosphino)oxy)biphenyl (44-BP), and 1,4-bis(((4,4' ,6,6'-tetra-tert-butyl-2,2'-bisphenoxy)phosphino)oxy)phenyl.

13. The hydroformylation process as set forth in claim 8, wherein the mono-phosphite ligand includes one or more selected from the group consisting of 4,4'-dimethoxy-6,6'-di-tert-butyl-2,2'-bisphenoxyphosphinoxy-benzene (BPP), 4,4', 6,6'-tetra-tert-butyl-2,2'-bisphenoxyphosphinoxy-benzene, 2,2'-bisphenoxyphosphinoxy-2,6-di-tert-butyl-4-methylbenzene and 2,2'-bisphenoxyphosphinoxy-2,6-di-tert-butylbenzene.

14. The hydroformylation process as set forth in claim 8, wherein the transition metal catalyst includes one or more compounds selected from the group consisting of cobalt carbonyl ($Co(CO)_8$), acetylacetonato dicarbonyl rhodium (Rh(AcAc)(CO)$_2$), acetylacetonato carbonyltriphenylphosphine rhodium (Rh(AcAc)(CO)(TPP)), hydrido carbonyltri(triphenylphosphine) rhodium (HRh(CO)(TPP)$_3$), acetylacetonato dicarbonyl iridium (Ir(AcAc)(CO)$_2$), and hydrido carbonyl tri(triphenylphosphine) iridium (HIr(CO)(TPP)$_3$).

15. The hydroformylation process as set forth in claim 8, wherein the olefin compound is a compound that is represented by the following Formula 5:

Formula 5 wherein $R_{22}$ and $R_{23}$ are each independently any one selected from the group consisting of hydrogen, an alkyl group having 1 to 20 carbon atoms, a fluorine group (—F), a chlorine group (—Cl), a bromine group (—Br), a trifluoromethyl group (—$CF_3$), and a $C_6$~$C_{20}$ phenyl group having 0 to 5 substituent groups, and the substituent group of the phenyl group is nitro (—$NO_2$), fluorine (—F), chlorine (—Cl), bromine (—Br), a methyl group, an ethyl group, a propyl group, or a butyl group.

16. The hydroformylation process as set forth in claim 15, wherein the olefin compound is one or more compounds selected from the group consisting of ethene, propene, 1-butene, 1-pentene, 1-hexene, 1-octene, and styrene.

17. The hydroformylation process as set forth in claim 8, wherein the solvent is one or more compounds selected from the group consisting of aldehydes; ketones; halogenated aromatics; ethers; paraffins; and paraffin hydrocarbons.

18. The hydroformylation process as set forth in claim 8, wherein the molar ratio of —CO to $H_2$ of the synthesis gas ($CO/H_2$) is in the range of 5:95 to 70:30.

19. The hydroformylation process as set forth in claim 8, wherein the hydroformylation reaction is performed at a temperature in the range of 20 to 180° C.

20. The hydroformylation process as set forth in claim 8, wherein the hydroformylation reaction is performed under pressure in the range of 1 to 700 bar.

21. A catalyst composition comprising:
a bis-phosphite ligand that is represented by the following Formula 1:

Formula 1

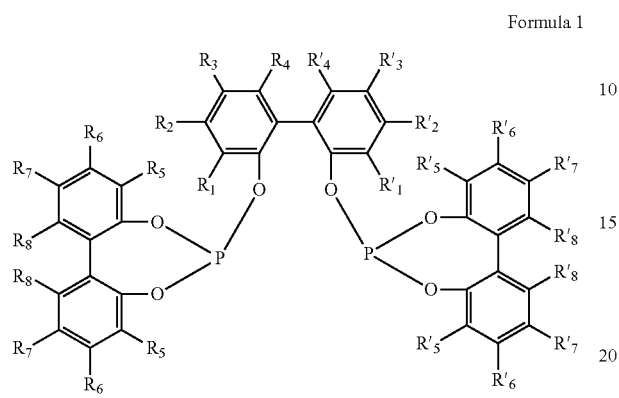

a mono-phosphite ligand that is represented by the following Formula 3:

Formula 3

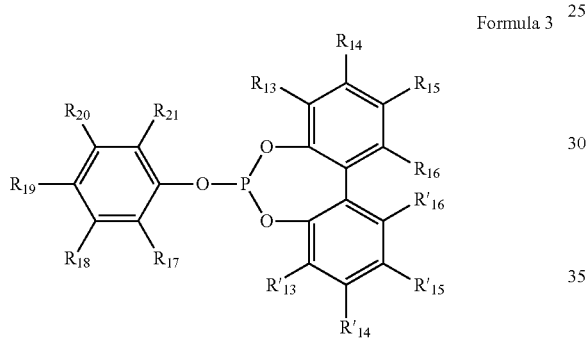

wherein $R_{13}$ to $R_{21}$ and $R_{13}'$ to $R_{16}'$ may be each independently different from or the same as each other, and are any one selected from the group consisting of hydrogen, $C_1$ to $C_{20}$ alkyl group, alkoxy group, aryl group, carboalkoxy group, aryloxy group, alkylcarbonyl group, amide group represented by the following formula —CONH, nitro group represented by the following formula —$NO_2$, halogen group, cyano group represented by the following formula —CN, silyl group represented by the following formula —$SiR_3$, wherein R is any one selected from the group consisting of hydrogen, alkyl group and alkoxy group, and sionyl group represented by the following formula —SR, wherein R is any one selected from the group consisting of hydrogen, alkyl group and alkoxy group, and a transition metal catalyst that is represented by the following Formula 4:

Formula 4

$$M\,(L^1)_x(L^2)_y(L^3)_z$$

wherein M is any one selected from cobalt (Co), rhodium (Rh) and iridium (Ir), $L^1, L^2$ and $L^3$ are each independently any one selected from hydrogen, CO, cyclooctadiene, norbornene, chlorine, triphenylphosphine and acetylacetonato, x, y and z are each independently in the range of 0 to 5, and x, y and z are not 0 at the same time.

* * * * *

UNITED STATES PATENT AND TRADEMARK OFFICE
CERTIFICATE OF CORRECTION

PATENT NO.        : 7,943,801 B2                                Page 1 of 1
APPLICATION NO.   : 12/595074
DATED             : May 17, 2011
INVENTOR(S)       : Jae-Hui Choi et al.

It is certified that error appears in the above-identified patent and that said Letters Patent is hereby corrected as shown below:

Column 1, line 9, "include" should read -- includes --.
Column 1, line 26, "one was" should read -- one, was --.
Column 1, line 29, "react ion" should read -- reaction --.
Column 1, line 30, "views" should read -- view --.
Column 1, line 48, "cobalt (Co)" should read -- a cobalt (Co) --.
Column 1, line 63, "respects" should read -- respect --.
Column 2, line 6, "Nitrogen-containing" should read -- nitrogen-containing --.
Column 2, line 39, "respects" should read -- respect --.
Column 7, line 50, "process, The" should read -- process, the --.
Column 15, line 36, "in respects" should read -- in respect --.
Column 17, line 26, "followin formula" should read -- following formula --.
Column 19, lines 22-23, "followinq" should read -- following --.
Column 20, line 19, "bisphenoxy)    phosphino)" should read
-- bisphenoxy) phosphino --.

Signed and Sealed this
Thirteenth Day of November, 2012

David J. Kappos
*Director of the United States Patent and Trademark Office*